US007179885B2

(12) United States Patent
Bouwstra et al.

(10) Patent No.: US 7,179,885 B2
(45) Date of Patent: Feb. 20, 2007

(54) SILVER-DISPERSING POLYPEPTIDES

(75) Inventors: Jan Bastiaan Bouwstra, Bilthoven (NL); Gertjan Bögels, Tilburg (NL); Yuzo Toda, Goirle (NL)

(73) Assignee: Fuji Photo Film B.V., Tilburg (NL)

( * ) Notice: Subject to any disclaimer, the term of this patent is extended or adjusted under 35 U.S.C. 154(b) by 632 days.

(21) Appl. No.: 10/451,897

(22) PCT Filed: Dec. 21, 2001

(86) PCT No.: PCT/NL01/00933

§ 371 (c)(1),
(2), (4) Date: Jun. 26, 2003

(87) PCT Pub. No.: WO02/052342

PCT Pub. Date: Jul. 4, 2002

(65) Prior Publication Data

US 2004/0048208 A1 Mar. 11, 2004

(30) Foreign Application Priority Data

Dec. 27, 2000 (EP) ................................. 00204775

(51) Int. Cl.
*C07K 14/78* (2006.01)
*G03C 1/005* (2006.01)
*G03C 1/047* (2006.01)

(52) U.S. Cl. ...................... 530/300; 430/230; 430/628; 530/350; 530/356

(58) Field of Classification Search ..................... None
See application file for complete search history.

(56) References Cited

U.S. PATENT DOCUMENTS 5,773,249 A 6/1998 Cappello et al. ........... 435/69.1

FOREIGN PATENT DOCUMENTS

| | | |
|---|---|---|
| EP | 0926543 | 6/1999 |
| EP | 1014176 | 6/2000 |
| EP | 1063565 | 12/2000 |
| WO | WO 9623866 | 8/1996 |

*Primary Examiner*—Jeffrey Edwin Russel
(74) *Attorney, Agent, or Firm*—Kilpatrick & Lockhart Preston Gates Ellis LLP

(57) ABSTRACT

Silver halide emulsions for photographic uses contain a nucleation peptiser having at least one region A of up to 100 amino acids. Region A can either consist of (i) at least two silver-binding amino acids and up to 98 amino acids between the two silver-binding amino acids, or can consist of (ii) a stretch of from 9 to 100 amino acids having a polarity corresponding to an average transfer free energy ΔF equal to or higher than +1.0 kcal/mol. The nucleation peptizer also has at least one region B (separated from region A) having at least 50 amino acids and having a polarity corresponding to an average transfer free energy equal to or lower than −1.0 kcal/mol and not containing methionine residues. The emulsion may also contain a growth peptiser having similar characteristics to the nucleation peptiser, but having a longer A region and a greater overall length.

24 Claims, No Drawings

SEQUENCE LISTING

```
<160> NUMBER OF SEQ ID NOS: 15

<210> SEQ ID NO 1
<211> LENGTH: 9
<212> TYPE: PRT
<213> ORGANISM: Artificial
<220> FEATURE:
<223> OTHER INFORMATION: Prior art recombinant synthetic polypeptide
      having a block copolymer structure of 4 different amino acids
<220> FEATURE:
<221> NAME/KEY: VARIANT
<222> LOCATION: (3)..(6)
<223> OTHER INFORMATION: X is selected from Met, Ile, His, Lys, Asn, Tyr
      and Gln

<400> SEQUENCE: 1

Gly Pro Xaa Gly Leu Xaa Gly Pro Arg
1               5


<210> SEQ ID NO 2
<211> LENGTH: 15
<212> TYPE: PRT
<213> ORGANISM: Artificial sequence
<220> FEATURE:
<223> OTHER INFORMATION: A 15-mer apolar peptide which is provided on
      page 6 as an example of the region A(n) of a peptizer according to
      the invention. This peptide has a polarity of +1.33.

<400> SEQUENCE: 2

Gly Pro Pro Gly Val Pro Gly Phe Ile Gly Phe Pro Gly Leu Pro
1               5                   10                  15


<210> SEQ ID NO 3
<211> LENGTH: 26
<212> TYPE: DNA
<213> ORGANISM: Artificial sequence
<220> FEATURE:
<223> OTHER INFORMATION: Primer HLP-PA-FW

<400> SEQUENCE: 3

gcgctcgaga aaagagaggc tgaagc                                          26


<210> SEQ ID NO 4
<211> LENGTH: 108
<212> TYPE: DNA
<213> ORGANISM: Artificial sequence
<220> FEATURE:
<223> OTHER INFORMATION: Primer OVL-PA-FW

<400> SEQUENCE: 4

gcgctcgaga aaagagaggc tgaagctggt ccacccggtg agccaggtaa cccaggatct      60

cctggtaacc aaggacagcc cggtaacaag ggttctccag gtaatcca                  108


<210> SEQ ID NO 5
<211> LENGTH: 110
<212> TYPE: DNA
<213> ORGANISM: Artificial sequence
<220> FEATURE:
<223> OTHER INFORMATION: Primer OVL-PA-RV

<400> SEQUENCE: 5
```

-continued tgagaacctt gtggaccgtt ggaacctggc tcaccaggtt gtccgttctg accaggttga 60
ccaggttgac cttcgtttcc tggttgacct ggattacctg gagaaccctt 110

<210> SEQ ID NO 6
<211> LENGTH: 24
<212> TYPE: DNA
<213> ORGANISM: Artificial sequence
<220> FEATURE:
<223> OTHER INFORMATION: Primer HLP-PA-RV

<400> SEQUENCE: 6
tgagaacctt gtggaccgtt ggaa 24

<210> SEQ ID NO 7
<211> LENGTH: 24
<212> TYPE: DNA
<213> ORGANISM: Artificial
<220> FEATURE:
<223> OTHER INFORMATION: Primer HLP-PB-FW

<400> SEQUENCE: 7
ttccaacggt ccacaaggtt ctca 24

<210> SEQ ID NO 8
<211> LENGTH: 115
<212> TYPE: DNA
<213> ORGANISM: Artificial
<220> FEATURE:
<223> OTHER INFORMATION: Primer OVL-PB-FW

<400> SEQUENCE: 8
ttccaacggt ccacaaggtt ctcagggtaa ccctggaaag aatggtcaac ctggatcccc 60
aggttcacaa ggctctccag gtaaccaagg ttcccctggt cagccaggta accct 115

<210> SEQ ID NO 9
<211> LENGTH: 108
<212> TYPE: DNA
<213> ORGANISM: Artificial
<220> FEATURE:
<223> OTHER INFORMATION: Primer OVL-PB-RV

<400> SEQUENCE: 9
gcgtctgcag tacgaattct attagccacc ggctggaccc tggtttcctg gtttaccttg 60
ttcacctggt tgaccagggt tacctggctg accaggggaa ccttggtt 108

<210> SEQ ID NO 10
<211> LENGTH: 26
<212> TYPE: DNA
<213> ORGANISM: Artificial
<220> FEATURE:
<223> OTHER INFORMATION: Primer HLP-PB-RV

<400> SEQUENCE: 10
gcgtctgcag tacgaattct attagc 26

<210> SEQ ID NO 11
<211> LENGTH: 18
<212> TYPE: DNA
<213> ORGANISM: Artificial
<220> FEATURE:
<223> OTHER INFORMATION: Primer HLP-H-FW

<400> SEQUENCE: 11

-continued

```
ccacccggtg agccagga                                                18


<210> SEQ ID NO 12
<211> LENGTH: 102
<212> TYPE: DNA
<213> ORGANISM: Artificial
<220> FEATURE:
<223> OTHER INFORMATION: Primer OVL-H-FW

<400> SEQUENCE: 12

ccacccggtg agccaggaaa ccctggtcac cacggtaacc aaggacagcc aggtaacgaa     60

ggtcaaccag gtcaggaagg taatcctgga aacgagggtc at                       102


<210> SEQ ID NO 13
<211> LENGTH: 102
<212> TYPE: DNA
<213> ORGANISM: Artificial
<220> FEATURE:
<223> OTHER INFORMATION: Primer OVL-H-RV

<400> SEQUENCE: 13

gccaccggct ggaccttggt taccgtggtg tccctgctca ccaggttgac ctggttgacc     60

ctcgtttcca ggttgaccgt gatgaccctc gtttccagga tt                       102


<210> SEQ ID NO 14
<211> LENGTH: 18
<212> TYPE: DNA
<213> ORGANISM: Artificial
<220> FEATURE:
<223> OTHER INFORMATION: Primer HLP-H-RV

<400> SEQUENCE: 14

gccaccggct ggaccttg                                                   18


<210> SEQ ID NO 15
<211> LENGTH: 161
<212> TYPE: PRT
<213> ORGANISM: Artificial
<220> FEATURE:
<223> OTHER INFORMATION: H-gelatin polypeptide is a hydrophobic gelatin
      with six histidine residues. The polypeptide is produced by
      expressing a synthetic gene encoding the peptide in Pichia, as
      described in Example 1.

<400> SEQUENCE: 15

Gly Pro Pro Gly Glu Pro Gly Asn Pro Gly Ser Pro Gly Asn Gln Gly
1               5                   10                  15

Gln Pro Gly Asn Lys Gly Ser Pro Gly Asn Pro Gly Gln Pro Gly Asn
            20                  25                  30

Glu Gly Gln Pro Gly Gln Pro Gly Gln Asn Gly Gln Pro Gly Glu Pro
        35                  40                  45

Gly Ser Asn Gly Pro Gln Gly Ser Gln Gly Asn Pro Gly Lys Asn Gly
    50                  55                  60

Gln Pro Gly Ser Pro Gly Ser Gln Gly Ser Pro Gly Asn Gln Gly Ser
65                  70                  75                  80

Pro Gly Gln Pro Gly Asn Pro Gly Gln Pro Gly Glu Gln Gly Lys Pro
                85                  90                  95

Gly Asn Gln Gly Pro Ala Gly Glu Pro Gly Asn Pro Gly His His Gly
            100                 105                 110

Asn Gln Gly Gln Pro Gly Asn Glu Gly Gln Pro Gly Gln Glu Gly Asn
        115                 120                 125
```

-continued

```
Pro Gly Asn Glu Gly His His Gly Gln Pro Gly Asn Glu Gly Gln Pro
    130                 135                 140

Gly Gln Pro Gly Glu Gln Gly His His Gly Asn Gln Gly Pro Ala Gly
145                 150                 155                 160

Gly
```

SILVER-DISPERSING POLYPEPTIDES

FIELD OF THE INVENTION

The subject invention is directed to biopolymers having silver-dispersing properties and to emulsions containing these biopolymers suitable for use in improved photographic products.

BACKGROUND OF THE INVENTION

The process of manufacturing photographic paper or film consists of coating several layers on top of either a laminated paper or a transparent polymer support like triacetate cellulose film. These layers comprise emulsion layers which contain the photosensitive silver halide crystals as an essential component, and intermediate layers which do not contain these photosensitive components.

The process of silver halide grain formation is controlled by the use of dispersing agents, usually referred to as peptisers. A nucleation peptiser is used during the precipitation of the silver halide grains to avoid uncontrolled coalescence. A growth peptiser is used during the growth process as dispersion stabiliser of the silver halide crystals, which functionality is also used between the different growth steps as well as after the end of the growth process when the crystals should remain stabilised under storage conditions. It is well known that tabular grains with high aspect ratio have several photographic advantages like increased sharpness, improved speed granularity relationships, more rapid developability and higher silver covering power (Research Disclosure Vol. 225 January 1983, Item 22534; EP-A-0.610.796). It has also been desired to produce tabular grains not only with high aspect ratio but also with a narrow grain size distribution, otherwise expressed as a desire for mono- or homodispersity.

Polypeptides are often used as peptisers in photographic manufacturing processes. Suitable polypeptides are collagen-like proteins such as gelatin in its numerous forms. Gelatin used in commercial processes has commonly been derived from animal sources such as animal bone and hide. Disadvantages of this material are the presence of impurities like non-collagenic protein, mucopolysaccharides, polynucleic acid and lipids and the fact that the nature of the composition is not clearly defined and thus not reproducible. In addition it is also unclear which components actually are required for optimal activity. The reproducibility of the photographic manufacturing process is questionable due to the lack of consistency of the gelatin composition used at various stages of the photographic manufacturing process.

U.S. Pat. Nos. 5,580,712, 5,670,616 and 5,710,252 are concerned with modified collagen-like polypeptides, their preparation and their application for photographic purposes. These patents disclose that collagen-like peptisers with silver binding strengths below 50 mV can lead to a high degree of thin tabular grain and illustrate this for a number of synthetically produced polypeptides with a length of 25 amino acids. These patents also disclose a polypeptide with a collagen-like structure which was produced using recombinant technology. The recombinant polypeptide is a synthetic polypeptide having a block copolymer structure consisting of 4 different amino acids (Gly, Pro, Glu and Gln), or a 25-mer peptide starting with Gly-Pro-$Xaa_1$-Gly-Leu-$Xaa_2$-Gly-Pro-Arg- (SEQ ID NO:1), wherein $Xaa_1$ and $Xaa_2$ are Met, Ile, His, Lys, Asn, Tyr or Gln.

EP applications 0926543 and 1014176 disclose the use of recombinant collagen-like biopolymers to produce silver halide emulsions wherein the tabular grains account for more than 75% of the total grain projected area. These collagen-like materials can be produced with high, economically feasible expression rates, without being susceptible to protease attack, and such recombinant material can be used in the preparation of photographic silver halide emulsion with improved photographic properties.

WO 9210567 discloses a helical structure wherein each 'screw' in the helix has a polar side and an apolar side such that the amphiphilic protein is folded flat covering the whole interface. JP-A 9-278793 discloses a similar structure in which hydrophobic and hydrophilic regions are located at opposite sides of the helix-structure. These patent applications are not concerned with for photographic applications, while the disclosed proteins are also not suitable for these photographic applications, because the interface surface would be covered to a large extent.

SUMMARY OF THE INVENTION

An objective of the present invention is to provide peptides having improved silver halide-dispersing properties to keep the silver halide crystals better dispersed.

Another objective of the invention is to provide photographic emulsions with a homogeneous grain-size distribution.

A further objective of the invention is to provide photographic emulsions with an increased number of tabular crystals.

Another objective of the invention is to reduce the costs associated with the use of recombinant peptisers.

Also an objective of the invention is to provide photographic emulsions with good dispersion stability of the silver halide crystals.

It has been found, surprisingly, that all these objectives are achieved by the use of a polypeptide as defined in the appending claims, as a nucleation peptiser in a silver halide emulsion. Thus, the invention relates to a silver halide emulsion containing a nucleation peptiser, said nucleation peptiser being a polypeptide comprising:

at least one region A(n) having a maximum length of 100 amino acids, said region A(n) either (i) being delimited by the extreme two of at least two silver-binding amino acids selected from histidine, lysine and arginine, not containing methionine or cysteine, or (ii) being defined by the maximum stretch of amino acids having a polarity corresponding to an average transfer free energy $\Delta F$ equal to or higher than +1.0 kcal/mol, said maximum stretch containing at least 9 amino acids but not containing cysteine or methionine; and at least one region B(n) comprising at least 50 amino acids and having a polarity corresponding to an average transfer free energy $\Delta F$ equal to or lower than −1.0 kcal/mol and not containing methionine or cysteine.

The invention also pertains to a nucleation peptiser and a growth peptiser to be used in such emulsions.

DESCRIPTION OF THE INVENTION

The invention provides bifunctional polypeptides to be used as nucleation peptisers, having functionally different regions A(n) and B, having strong affinity to silver halides in regions A(n) and dispersing properties without strong affinity for silver halides in regions B. The invention also provides similar bifunctional polypeptides to be used as growth peptisers having strong affinity for silver halides in regions A(g) and dispersing properties without strong affinity for silver halides in regions B, as well as the combined use of such nucleation and growth peptisers in photographic silver halide emulsions.

The polypeptides are preferably recombinant polypeptides. The invention also provides silver halide emulsions containing such bifunctional polypeptides. The polypeptides of the invention have the advantage over prior art polypeptides in that good dispersion stability is provided at lower concentrations than are necessary with conventional polypeptides or proteins, without undesired shielding off of the silver halide crystal surface.

The function of region A(n) is to bind the polypeptide to the silver halide surface via a strong binding to silver ions. In principle this functionality can be provided by interactions involving amino acids having elements capable of sharing free electrons, such as sulphur and nitrogen, or by hydrophobic interactions involving hydrophobic amino acids such as isoleucine, leucine, valine and phenylalanine (and analogous non-natural amino acids such as norleucine), or by a combination of these interactions. It is to be understood that when this text reads 'binding to silver halide surface' means binding to silver ions.

Methionine and histidine have a high affinity to silver halide. It should be noted where reference is made to methionine and histidine, these are the unmodified amino acids. Modified amino acids having lost part or all of their silver-binding capacity such as oxidised methionine are not included. Other amino acids having a side-group which contains an amino group, like lysine or arginine, are also suitable. Non-natural or derivatised amino acids having silver-binding properties may also be used, such as amino acids with side groups like carboxy or amino groups in Arg, Asp, Asn, Glu, Gln, Lys, which side groups have been modified by linking with:

- aminotriazines and aminopyrimidines (e.g. 2,4-diamino-1,3,5-triazine, 4-amino-pyrazolo[3,4,d]pyrimidine, 4,6-diaminopyrimidine, 4,6-bis(methylamino)pyrimidine, 4,5,6-triaminopyrimidine, 5,6-diamino-4-(N-methylamino)pyrimidine, 4,5,6-tri-(N-methylamino)pyrimidine, 4,6-diamino-5-(N,N-dimethylamino) pyrimidine, 4,6-diamino-5-(N-hexylamino)pyrimidine,
- aminoazaindenes (e.g. adenine, guanine),
- iodophenols (e.g. 2,6-diiodophenol, 2,4,6-triiodophenol, 2,6-diiodo-4-nitrophenol),
- as described in EP 0737887, p.3, an organic compound having at least one nitrogen atom having a resonance-stabilised $\pi$-electron pair, comprising: nitrogen-containing heterocyclic compounds, such as substituted or unsubstituted and saturated or unsaturated heterocyclic compounds having nitrogen as a sole heteroatom (e.g. pyridine, pyrrole, pyrrolidine, quinoline) or having a nitrogen atom and at least one additional heteroatom (e.g. imidazole, imidazoline, pyrazole, oxazole, piperazine, triazole, tetrazole, oxadiazole, oxatriazole, dioxazole, pyrimidine, pyrimidazole, pyrazine, triazine, tetrazine, benzimidazole).

Region A(n) of the nucleation peptiser comprises at least 2 amino acids, up to a maximum length of 100 amino acids, more preferably from 3 to 50 amino acids or even from 4 or even from 6, up to 20 amino acids. Region A comprises at least two amino acids which bind strongly to silver ions. The presence of at least two of such groups provides the benefit of polymer inertia, that is that both, or all, binding amino acids should desorb simultaneously in order to desorb the polypeptide. A higher number of binding groups reduces the chance that the polypeptide desorbs as a whole. It is preferred that a stretch of at least half the size of said maximum length containing region A(n) does not contain silver-binding amino acids outside said region A(n). More preferably, region A is defined as the largest area having two terminal silver-binding amino acids within a stretch of amino acids of the maximum length (100, 50 or 20), i.e a stretch of the maximum length containing A(n) does not contain silver-binding amino acids outside said region A(n). If there is a choice, within a given amino acid sequence, of defining a region A on the basis of two or more silver-binding amino acids, region A is defined as the largest unfractioned stretch between—and including—two silver-binding amino acids. However, in case a polypeptide comprises, for example, of a stretch of about 100 amino acids in which two regions A are located near the C-terminal and N-terminal side of that stretch and these regions A are separated by an area B, the preferred definition as described above is not intended to exclude such a structure.

Preferably the amino acid binding strongly to silver ions is histidine. Methionine has the strongest binding to silver ions. Characteristic for methionine is that this binding is independent of pH, and thus can be applied over a wide pH-range. However, the strength of the silver binding is such that methionine is not an ideal silver-binding amino acid in photographic emulsions. Only when other amino acids are not available as silver binders, in particular at low pH values (below about 5.5, especially below 5.0), methionine is to be used in the peptisers of the present invention. At higher pH values, it is preferred that there is no methionine in the silver-binding region. When building recombinant or synthetic structures one might include methionine in a binding area A and modify said methionine, for example by oxidation, by which methionine looses its capacity to bind to silver ions. Such a possibility is not contemplated since the recombinant or synthetic methods provide the opportunity to avoid the presence of methionine. Although the binding of histidine to silver ions is less strong than methionine, it has an additional feature in that the binding strength can be regulated by varying the pH. This provides the possibility to match the binding strength of the recombinant polypeptide comprising histidines to each stage of the process of manufacturing silver halide emulsions. Preferably, at least two histidines, more preferably at least three are present in region A(n). At higher pH values, of 8.0 or higher, especially 8.5 or higher, free-nitrogen-containing amino acids like lysine or arginine can be used for binding to silver ions. At these high pH values, these amino acids lysine and arginine should preferably not be present in region B (n). The required amino acid content of the regions A and B in the various embodiments is as follows:

| | pH < 5.5 | 5.0 < pH < 8.5 | pH > 8.0 |
|---|---|---|---|
| amino acids required in A(n) (i) | ≦2 Met | ≧2 His | ≧2 His, Lys or Arg |
| amino acids required in A(g) (i) | 2 ≦ Met ≦ 4 | ≧2 Met, His | ≧2 Met, His, Lys or Arg |
| amino acids required in A(n or g) (ii) | ≧2 Ile, Leu, Val or Phe | ≧2 Ile, Leu, Val or Phe | ≧2 Ile, Leu, Val or Phe |
| amino acids not present in A(n) | more than 2 Met; Cys | Met, Cys | Met, Cys |
| amino acids not present in A(g) | more than 4 Met; Cys | more than 2 Met; Cys | more than 2 Met; Cys |

-continued

| | pH < 5.5 | 5.0 < pH < 8.5 | pH > 8.0 |
|---|---|---|---|
| amino acids not present in B(n or g) | Met, Cys | Met, Cys, | Met, Cys |

Region A(n) may be of varying polarity, while region B(n) should be relatively polar. The polarity of the regions of the polypeptides to be used according to the invention can be defined with reference to the transfer free energy (TFE) of the individual amino acids constituting the polar and apolar parts of the polymer, respectively. This transfer free energy (ΔF) is the energy (in kcal/mole) of the amino acid residue in an α-helix to be transferred from the membrane interior to the water phase. These energy values as defined by Engelman et al, *Ann. Rev. Biophlys. Biophys. Chem.* 15 (1986), 330, are summarised in the table below.

| | | | | | | | | | | |
|---|---|---|---|---|---|---|---|---|---|---|
| a.a. | Phe | Met | Ile | Leu | Val | Cys | Trp | Ala | Thr | Gly |
| ΔF | 3.7 | 3.4 | 3.1 | 2.8 | 2.6 | 2.0 | 1.9 | 1.6 | 1.2 | 1.0 |
| a.a. | Ser | Pro | Tyr | His | Gln | Asn | Glu | Lys | Asp | Arg |
| ΔF | 0.6 | −0.2 | −0.7 | −3.0 | −4.1 | −4.8 | −8.2 | −8.8 | −9.2 | −12.3 |

The polarity of a given amino acid sequence is defined herein as the average transfer free energy per amino acid of the sequence, which equals the sum of the product of the number of individual amino acids and the transfer free energy of each amino acid, divided by the total number of amino acids. In a formula:

$$Polarity=(\Sigma n_i*\Delta F_i)/n_t$$

wherein $n_i$ is the number of each individual amino acid, $\Delta F_i$ is the transfer free energy of the corresponding amino acid, and $n_t$ is the total number of amino acids. As an example, a 15-mer apolar peptide having the following amino acid sequence:

Gly Pro Pro Gly Val Pro Gly Phe Ile Gly Phe Pro Gly Leu Pro (SEQ ID NO:2) has the following amino acid composition: 5 Gly+5 Pro+1 Val+2 Phe+1 Ile+1 Leu, and hence it has the following polarity (in kcal/mole per amino acid):

$$(5*1.0+5*-0.2+1*2.6+2*3.7+1*3.1+1*2.8)/15=19.9/15=+1.33$$

Apolar sequences generally have positive polarity values, whereas polar sequences have negative polarity values.

The polarity of region A(n) may be low, corresponding to a positive average TFE value, i.e. ΔF>0. In case of sufficient hydrophobicity (low polarity), the presence of one or two specifically silver-binding amino acids in the nucleation peptiser can be dispensed with. The average ΔF should then be at least +1.0 or +1.3 or higher. Thus, region A(n) is defined by either by (i) two (most far apart) silver-binding amino acids and from 0 up to 98 intervening amino acids between these two silver-binding amino acids, which intervening amino acids may comprise further silver-binding amino acids as described above, or by (ii) a stretch of at least 9, up to 100 amino acids having an average ΔF of +1.0 kcal/mol and containing at least two amino acids selected from Ile, Leu, Val, Phe, and no Met or Cys. It is preferred in embodiment (ii) that region A(n) has an average ΔF of at least +1.3 or higher or has a length of at least 16 amino acids, or both. The preferred length of region A(n) (ii) is between 16 and 100, most preferred between 26 and 50 amino acids.

The advantage of the recombinant polypeptide of this invention is that it has, besides a region A which binds to the silver halide surface, a region B which has, unlike region A, a low binding to the silver halide surface. A sufficient number of polar amino acids should be present in region B so that the average transfer free energy per amino acid is −1.0 kcal/mol or lower, preferably −1.3 kcal or lower. It is preferred that the high polarity is more or less uniform over region B. Therefore, region B preferably has a moving polarity corresponding to a moving average transfer free energy over 20 amino acids equal to or lower than +0.5 kcal/mol, preferably equal to or lower than +0.1 kcal/mol. Advantageously, region B contains at least two acidic amino acids (Glu, Asp). Lysine and arginine can be used at pH well below their isoelectric point—in particular at pH values between 3 and 8—in which case they contribute to the polar character of region B substantially without binding to the silver halide surface. It is preferred that region B contains less than three, preferably less than two, most preferably no silver-binding amino acids (His, Lys, Arg at pH>8.; His at pH>5.5; Met and Cys at all pH's).

In order to provide adequate steric repulsion, i.e. repulsion between silver halide particles on which polypeptides are absorbed, region B comprises at least 50 amino acids, preferably from 100 to 600 amino acids. The low-binding region B extends from the binding site into the dispersion medium thus providing protection against coagulation by steric repulsion. This function can also be obtained by natural, recombinant or synthetic polypeptides that do not by design have functional areas. However, these materials have a serious drawback compared to the invention recombinant polypeptide.

The binding groups of conventional polypeptides, like gelatin, are more or less randomly distributed over the polypeptide chain. As a result, at low concentrations the conventional polypeptides will adsorb onto the silver halide surface in a flat orientation with respect to the silver halide surface. Although a non-binding region between binding groups may form some loops, the steric repulsion at low concentrations of conventional polypeptides is negligible. In order to obtain an acceptable degree of steric repulsion using the conventional materials as described above, adsorbed layers of the conventional polypeptide should be present before enough free polypeptide 'tails' extending into the dispersion medium can exist. This has the disadvantage that much of the expensive polypeptide material is used that does not contribute to the desired effect of steric repulsion. A further disadvantage is that the conventional polypeptides effectively shield the surface of the crystal, obstructing processes occurring at that surface, like twinning. The recombinant polypeptide of the invention has the advantage that already at low concentrations the material provides steric repulsion without shielding off the crystal surface.

Region A may preferably be a single region coupled to a single region B (A-B). It may also be a single region A coupled to two regions B (B-A-B), or a multiple region coupled to one or more regions B (A-B-A, A-B-A-B, B-A-B-A-B), etc. Regions A and B may also be separated by small indifferent regions not complying with either (A) or (B), i.e. being non-silver-binding regions having lower polarity (ΔF>−0.5) of up to e.g. 30 amino acids. As follows from the examples above, there are preferably no more than two regions A, more preferably only one. Where there are two regions A, they should be separated by a region B, and possibly one or two short indifferent regions. Preferably no, or only short (<10 amino acids) indifferent non-A, non-B regions are present as terminal regions. Most preferably, the entire polypeptide does not contain non-A, non-B regions, or only very small ones (6 amino acids or less). Where a region of one type is coupled to one or two (or even three) regions of another type, this may be a "normal" peptide bond, or a coupling involving a crosslink of the collagen type, i.e. by chemical coupling of hydroxylysine (obtained by oxidation of a lysine residue) from each chain which is coupled. The total polypeptide may be from 52 to about several thousands amino acids in length, preferably from 75 to about 1200 amino acids (about 8 to 130 kDa), most preferably from about 100 to 600 amino acids (about 11 to 65 kDa).

The polypeptide may be any type of polypeptide meeting the requirements as to silver-binding and polarity in different regions A and B as defined above. A useful type of polypeptide that can used in the present invention is a collagen-type polypeptide. A collagen-like polypeptide is understood to be a polypeptide having at least 21 amino acids, or at least 50%, preferably at least 80%, of the total number of amino acids in triplet form, each triplet having the sequence GXY, in which G is glycine, X is any amino acid, and Y is amino acid. Preferably at least 17%, up to 67% of the amino acids X and Y are proline; in particular, at least half of the triplets has the sequence GXP or GPY.

The growth peptiser is a polypeptide comprising at least one region A(g) consisting of at least two silver-binding amino acids, the extreme two thereof delimiting region A(g), and comprising more than 100 amino acids up to a maximum of ⅓ part of the total number of amino acids. Preferably the amino acids of region A(g) have a low polarity corresponding to an average TFE equal to or higher than +0.5 kcal/mol. The growth peptiser should always contain at least two silver-binding amino acids. Preferably, there are more than two, of which at least two are histidines and of which no more than three, more preferably no more than two are methionines. The growth peptiser also comprises at least one region B(g) containing at least 50 amino acids, preferably at least 100 or even at least 200 amino acids, and having a polarity corresponding to an average TFE lower than −1.0 kcal/mol, preferably equal to or lower than −1.3 kcal.mol, and not containing methionine or cysteine. Thus, except for the requirements for methionine which are more strict for a nucleation peptiser, the properties of the growth peptiser largely correspond to those of the nucleation peptiser described above, but for a larger size: it is preferred that the growth peptiser has a length of at least 180, up to several thousands of amino acids, more preferably at least 240 amino acids, up to e.g. 1800 amino acids.

A silver halide emulsion according to the invention suitably is one wherein the recombinant polypeptide is substantially free from helical structure. The recombinant polypeptide is suitably free from any helical structure. Helix structures generally do not occur at higher temperatures of about 35° C. as applied in the manufacturing of silver halides emulsions. The absence of the (triple) helical structure is advantageous, because the nucleation of silver halides can be performed at a wider temperature range, more specifically at lower temperatures (15–25° C.) than the traditional temperature during nucleation (about 35° C.); usually at these lower temperatures helix structures are formed. Nucleation at lower temperatures is desired in the art of manufacturing silver halide to emulsions because this contributes to a narrower silver halide grain size distribution. A further advantage of the absence of helical structure is that at low temperatures the polypeptide extends further from the silver halide surface into the dispersion medium. Dispersion stability depends, among other factors, on the length of the polypeptide chain extending from the silver halide surface into the dispersion medium.

It is a preferred embodiment of the invention that the recombinant polypeptide of both the nucleation peptiser and the growth peptiser of the silver halide emulsion is free of hydroxyproline as this ensures the absence of (triple) helix formation. Thus, when produced by expression of genes encoding the polypeptides, the organism containing the gene does preferably not express a proline-hydroxylating enzyme. Preferably the polypeptide of the invention does not contain cysteine residues, since cysteine binds too strong to silver and may lead to undesired folding or coupling of the polypeptide, thus hampering the dispersing efficiency. Likewise, the polypeptide preferably does not contain methionine residues, except at acidic pH (below 5.5), where the nucleation peptizer may contain up to two methionines and where the growth peptizer may contain up to 4 methionines. If the presence of cysteine (and methionine) cannot be easily avoided, it is preferred that these amino acids are modified, e.g. by oxidation and/or alkylation, so as to suppress their folding or complexing activities.

The polypeptides of the invention can conveniently be used as a nucleation peptiser, a growth peptiser or both, depending on their length. During nucleation too strong binding should be avoided as recognised for example in EP 0228256, EP 0843208, according to which teachings the binding should be equivalent to less than 30 micromol of methionine per gram polypeptide.

In a preferred embodiment the polypeptide of the invention is used to manufacture thin tabular silver halide crystals having (111) major faces. As a nucleation peptiser said recombinant polypeptide has the advantage that good dispersion stability is obtained without shielding off the silver halide surfaces. As taught in, for example, U.S. Pat. No. 5,087,555, the amount of tabular crystals is determined by controlled double twinning, an event occurring at the crystal surfaces. During nucleation there is a preference to use histidine as the binding amino acid because this offers the possibility to tune the binding strength by adjusting pH. As is also taught in U.S. Pat. No. 5,087,555, binding strength has an effect on twinning. A further advantage is that at the same time the polypeptide of the invention provides a way to control binding strength at later stages in the process of manufacturing silver halide emulsions. After nucleation the pH can be adjusted to the optimum binding strength for ripening, and at a later stage binding strength. can be maximised to achieve optimal storage time.

Using a collagen-like polypeptide of the invention has also advantage over conventional collagen-like materials for other processes which occur at the crystal interface. Spectral sensitiser adsorption is affected by adsorbed collagen. Using the invention collagen-like polypeptide provides a method to adsorb more sensitiser on the surface. The functional advantage of creating specific separated areas, each area having its functionality is advantageously combined with other well-appreciated advantages of recombinant collagen-like polypeptides like narrow molecular weight distribution, high reproducibility without contaminations, less susceptible to biodegradation.

In another embodiment the polypeptide has a region A with strong binding to silver ions and a region B which comprises amino acids in which the side group is modified. A carboxylic acid group attached to a photographically useful group can be activated resulting in a so-called activated carboxyl. As taught in patents EP 0576911 and EP 0487686, said activated carboxyl reacts with a pendant amino group of the amino acids present in said region B (e.g. lysine), forming an amide bond. It is also possible to activate the pendant carboxyl groups of amino acids present in said region B (e.g. glutamic or aspartic acid) by adding a carboxyl activator, after which photographically useful groups comprising an amino group will be linked to the amino acids by forming an amide bond. Photographically useful groups which may thus be linked to said region B include developer scavengers, UV-light absorbers, optical brighteners and the like. This is advantageous over the prior art in that such photographically useful compounds are conventionally dissolved into photographic emulsion layers or are first dissolved in hydrophobic solvents and subsequently dispersed into a photographic emulsion layer. These conventional methods use environmental unfriendly solvents and have the problem of undesired diffusion of the photographic useful compounds. Other modifications of said region B are possible, like succination, phtalation, vinylsulfonation, allylsulfobetaination, fluorination, the advantages of which are described in for example patents DE 4231278; U.S. Pat. No. 5,087,694; U.S. Pat. No. 3,132,945; U.S. Pat. No. 5,316,902 or in The Imaging Science Journal, Vol 45, no3/4, 1997, 102–106; S. J. Brand, Photographic Gelatin, Royal Photographic Society, 1987, 206.

The polypeptides of the invention can be produced by recombinant methods as disclosed in EP-A-0926543 and EP-A-1014176. Thus the collagen-like polypeptides can be produced by expression of nucleic acid sequence encoding such polypeptide by a suitable microorganism. The process can suitably be carried out with a fungal cell or a yeast cell. Suitably the host cell is a high expression host cells like *Hansenula, Trichoderina, Aspergillus, Penicillium, Neurospora* or *Pichia*. Fungal and yeast cells are preferred to bacteria as they are less susceptible to improper expression of repetitive sequences. Most preferably the host will not have a high level of proteases that attack the collagen structure expressed. In this respect *Pichia* offers an example of a very suitable expression system.

Preferably the micro-organism is free of active post-translational processing mechanism for processing collagen like sequences to fibrils thereby ensuring absence of helix structure in the expression product. Also such a process can occur when the micro-organism is free of active post-translational processing mechanism for processing collagen like sequences to triple helices and/or when the nucleic acid sequence to be expressed is free of procollagen and telopeptide encoding sequences. The host to be used does not require the presence of a gene for expression of prolyl-4-hydroxylase, the enzyme required for collagen triple helix assembly contrary to previous suggestions in the art concerning collagen production. The selection of a suitable host cell from known industrial enzyme producing fungal host cells specifically yeast cells on the basis of the required parameters described herein, rendering the host cell suitable for expression of recombinant collagen according to the invention suitable for photographic applications, in combination with knowledge regarding the host cells and the sequence to be expressed will be possible by a person skilled in the art.

Alternatively, the polypeptide of the invention may be produced wholly or partly by chemical means, i.e. by coupling of individual amino acids or amino acid chains using suitable chemical peptide coupling methods. For example, a recombinantly produced polypeptide containing region B, may chemically coupled to an oligopeptide or poly-peptide of region B to produce the polypeptide of the invention. Although chemical synthesis is generally more complicated than recombinant product, it may allow combination of different types of subunits, possibly containing non-natural or derivatised amino acids.

The silver halide of the present invention, preferably used in photographic emulsion layers of a light-sensitive material, is silver iodobromide, silver iodochloride or silver iodochlorobromide containing about 30 mol % or less silver iodide. A particularly preferable silver halide is silver iodobromide or silver iodochlorobromide each containing about 2 mol % to about 10 mol % of silver iodide. The silver halide grains contained in the photographic emulsion may be in the form of regular crystals, such as cubes, octahedrons and decatetrahedrons, irregular crystals, such as spheres and tabulars, crystals having defects such as twin planes, or composition shapes thereof. The grain size of the silver halide may range from fine grains having a grain diameter of about 0.2 micrometer or less to large grains having a diameter of the projected area of a grain up to about 10 micrometer. Further, the silver halide emulsion may be a polydisperse emulsion or a monodisperse emulsion, but is preferably a monodisperse emulsion. The silver halide photographic emulsion useable in the present invention can be prepared by the methods described, for example, in Research Disclosure (hereinafter abbreviated RD) No. 17643 (December 1978), pages 22–23, "I. Emulsion Preparation and Types"; RD No. 18716 (November 1979), page 648, and RD No. 307105 (November 1989), pages 863–865; P. Glafikides, "Chimie et Physique Photographiques", Paul Montel, 1967; G. F. Duffin, "Photographic Emulsion Chemistry", Focal Press 1966; and V. L. Zelikman et al., "Making and Coating Photographic emulsion", Focal Press, 1964. Also preferable is the monodisperse emulsion described in U.S. Pat. No. 3,574,628, U.S. Pat. No. 3,655,394 and GB 1,413,748.

Further, tabular grains having an aspect ratio of about 3 or more can also be used in the present invention. The tabular grains can be easily prepared by the methods described in Gutoff, "Photographic Science and Engineering", Vol. 14, pp. 248–257 (1970); U.S. Pat. Nos. 4,434,226; 4,414,310; 4,433,048 and 4,439,520, and GB patent 2,112,157. The crystal structure may be uniform, may have different halogen compositions in its interior and exterior, or may be a layered structure. Alternatively, silver halide having different compositions may be joined by an epitaxial junction, or a compound other than a silver halide such as silver rhodanide or lead oxide may be joined. A mixture composed of grains having various crystal forms may also be used.

The above-mentioned emulsion needs to be a negative-type emulsion, although it may be of a surface latent image type which forms a latent image mainly on the surface of a the grains, an inner latent image type which forms a latent image inside the grains, or other type which forms a latent image both inside and outside the grain. The emulsion belonging to the inner latent image type may be of the inner latent image type having a core/shell structure described in JP-A-63-264740, the method for making which emulsion is described in JP-A-59-133542. The thickness of the shell for this emulsion is preferably 3 to 40 nm and most preferably 5 to 20 nm, although the thickness varies depending on processing conditions for development and the like. Prior to the use of the light-sensitive material of present invention, the silver halide usually undergoes a chemical ripening, a physical ripening and spectral sensitising steps. The additives which are used at such steps are described in RD No. 17643, RD No. 18716 and RD No. 307105.

EXAMPLES

Example 1

Recombinant Collagen-like Peptide

General molecular-biological techniques

Cloning procedures were performed essentially according to Maniatis et al. [Maniatis T., Fritsch, E. F. & Sambrook, J. (1982) Molecular cloning: A laboratory manual. Cold Spring Harbor Laboratory, Cold Spring Harbor, N.Y.]. Plasmid DNA was isolated using Wizard Plus SV miniprep, or Qiagen midiprep systems. DNA was isolated from agarose gels using the QIAquick Gel Extraction Kit (Qiagen). All enzymes used were from Amersham Pharmacia Biotech unless otherwise stated and were used according to the recommendations of the manufacturer. All procedures involving the handling and transformation of *Pichia pastoris* were essentially performed according to the manual of the *Pichia* Expression Kit (Invitrogen) [Manual of the *Pichia* Expression Kit Version E (Invitrogen, San Diego, Calif., USA)].

Construction of pPIC9-H1

A synthetic gene encoding a hydrophilic gelatin with six histidine residues (referred to hereafter as "H-gelatin") was designed to have the codon usage of *Pichia pastois* highly expressed genes (Sreekrishna, K. and Kropp, K. E. (1996) *Pichia pastoris,* Wolf, K.(Ed), *Non conventional yeasts in biotechnology. A handbook,* Springer-Verlag, pp. 6/203–6/253).

Two separate PCR reactions were performed, using the following oligonucleotides:

10.1 pmol OVL-PA-FW, 1 pmol OVL-PA-RV, 50 pmols HLP-PA-FW and 50 pmols HLP-PA-RV.

11.1 pmol OVL-PB-FW, 1 pmol OVL-PB-RV, 50 pmols HLP-PB-FW and 50 pmols HLP-PB-RV.

Oligonucleotide sequences were as follows:

```
3 HLP-PA-FW: 5'-GCGCTCGAGA AAAGAGAGGC TGAAGC-3'  (SEQ ID NO:3)

OVL-PA-FW: 5'-GCGCTCGAGA AAAGAGAGGC TGAAGCTGGT  (SEQ ID NO:4)

CCACCCGGTG AGCCAGGTAA CCCAGGATCT CCTGGTAACC

AAGGACAGCC CGGTAACAAG GGTTCTCCAG GTAATCCA-3'

OVL-PA-RV: 5'-TGAGAACCTT GTGGACCGTT GGAACCTGGC  (SEQ ID NO:5)

TCACCAGGTT GTCCGTTCTG ACCAGGTTGA CCAGGTTGAC

CTTCGTTTCC TGGTTGACCT GGATTACCTG GAGAACCCTT-3'

HLP-PA-RV: 5'-TGAGAACCTT GTGGACCGTT GGAA-3'     (SEQ ID NO:6)

HLP-PB-FW: 5'-TTCCAACGGT CCACAAGGTT CTCA-3'     (SEQ ID NO:7)

OVL-PB-FW: 5'-TTCCAACGGT CCACAAGGTT CTCAGGGTAA  (SEQ ID NO:8)

CCCTGGAAAG AATGGTCAAC CTGGATCCCC AGGTTCACAA

GGCTCTCCAG GTAACCAAGG TTCCCCTGGT CAGCCAGGTA

ACCCT-3'

OVL-PB-RV: 5'-GCGTCTGCAG TACGAATTCT ATTAGCCACC  (SEQ ID NO:9)

GGCTGGACCC TGGTTTCCTG GTTTACCTTG TTCACCTGGT

TGACCAGGGT TACCTGGCTG ACCAGGGGAA CCTTGGTT-3'

HLP-PB-RV: 5'-GCGTCTGCAG TACGAATTCT ATTAGC-3'   (SEQ ID NO:10)
```

The 50 μl PCR reactions were performed in a GeneAmp 9700 (Perkin-Elmer) and contained 0.2 mM dNTP's (Pharmacia), 1×Pwo buffer (Eurogentec) and 1.25 U Pwo polymerase (Eurogentec). Reaction 1 involved 18 cycles consisting of 15 seconds at 94° C. and 15 seconds at 72° C. Reaction 2 involved a touchdown PCR, whereby each cycle consisted of 15 seconds at 94° C., 15 seconds at the annealing temperature and 15 seconds at 72° C. The annealing temperature was lowered from 72° C. to 68° C. in the first 5 cycles, after which 20 additional cycles at an annealing temperature of 67° C. were performed.

The PCR products were isolated from agarose gel. 0.3 pmols of each fragment and 50 pmols of the outer primers HLP-PA-FW and HLP-PB-RV were subjected to overlap extension PCR. 25 cycles consisting of 15 seconds at 94 ° C., 15 seconds at 67° C. and 15 seconds at 72° C. were performed. The resulting 0.3 kb PCR fragment was digested with XhoI/EcoRI and inserted in cloning vector pMTL23. An errorless clone (referred to hereafter as "pMTL23-P") was selected by verification of the sequence by automated DNA sequencing.

An additional PCR reaction was performed using the following oligonucleotides:

1 pmol OVL-H-FW, 1 pmol OVL-H-RV, 50 pmols HLP-H-FW and 50 pmols HLP-H-RV.

Oligonucleotide sequences were as follows:

```
HLP-H-FW: 5'-CCACCCGGTG AGCCAGGA-3'           (SEQ ID NO:11)
OVL-H-FW: 5'-CCACCCGGTG AGCCAGGAAA CCCTGGTCAC  (SEQ ID NO:12)
CACGGTAACC AAGGACAGCC AGGTAACGAA GGTCAACCAG
GTCAGGAAGG TAATCCTGGA AACGAGGGTC AT-3'
OVL-H-RV: 5'-GCCACCGGCT GGACCTTGGT TACCGTGGTG  (SEQ ID NO:13)
TCCCTGCTCA CCAGGTTGAC CTGGTTGACC CTCGTTTCCA
GGTTGACCGT GATGACCCTC GTTTCCAGGA TT-3'
HLP-H-RV: 5'-GCCACCGGCT GGACCTTG-3'           (SEQ ID NO:14)
```

The 50 μl PCR reactions were performed in a GeneAmp 9700 (Perkin-Elmer) and contained the oligos indicated above and 25 μl of High Fidelity PCR Master (Roche). The reaction involved 18 cycles consisting of 15 seconds at 94° C., 15 seconds at 60° C. and 15 seconds at 72° C. The 0.18 kb PCR product was isolated from agarose gel and T/A cloned into vector pGEM-T Easy (Promega). An errorless clone was selected by verification of the sequence by automated DNA sequencing. The vector was then digested with DraIII/Van91I. The resulting 0.18 kb fragment was isolated from agarose gel and cloned into Van91I digested, dephosporylated pMTL23-P. The resulting vector was cut with EcoRI/XhoI, after which the insert was cloned into EcoRI/XhoI digested *P. pastoris* expression vector pPIC9, to yield vector pPIC9-H1.

The encoded amino acid sequence of the mature (processed) H-gelatin is as follows:

```
  1 GPPGEPGNPG SPGNQGQPGN KGSPGNPGQP (SEQ ID NO:15)
 31 GNEGQPGQPG QNGQPGEPGS NGPQGSQGNP
 61 GKNGQPGSPG SQGSPGNQGS PGQPGNPGQP
 91 GEQGKPGNQG PAGEPGNPGH HGNQGQPGNE
121 GQPGQEGNPG NEGHHGQPGN EGQPGQPGEQ
151 GHHGNQGPAG G
```

Molecular weight: 15.1 kDa, isoelectric point: 5.1. Region A at pH<8: amino acids 110–153; ΔF=–2.3; region B: amino acids 1–109; ΔF=–1.4.

Example 2

Comparative

Emulsion A is made in an agitated 4 L vessel starting from a solution containing 0.5 g/l of a regular bone gelatin, G-PB #8080, from PB, Tessenderlo, Belgium, and 1.19 g/l KBr bringing the initial pBr to a value of 2.0.

The nucleation is performed at a temperature of 40° C. and the pH is 3.5. By a double jet method solutions of silver nitrate and potassium bromide are added in 20 seconds simultaneously at a flow rate of respectively 0.062 and 0.063 mol/min. After the nucleation a quantity of 0.021 mol silver has been added. After the nucleation the pBr is changed to 1.8 and the temperature is gradually increased to a value of 60° C. with a rate of 4° C./min. The emulsion is kept at this temperature for 20 min after which a solution of the same gelatin, containing 33 g, is added to bring the concentration of the gelatin up to 25 g/l. The pH is adjusted to a value of 5.5. Two minutes after this gelatin addition the growth starts by accelerated double jet method by adding in 50 minutes 1.07 mol silver and sufficient potassium bromide to keep the potential during the growth constant at a value of 0 mV versus a calomel electrode. The final flow rate is 4× higher than the initial flow rate.

The resulting emulsion is analysed by Disk Centrifuge (CPS Instruments Inc.) and by TEM replica. The results are summarised in table 1.

Example 3

Comparative

Emulsion B is made by the same method as emulsion A except that the nucleation is performed at a temperature of 15° C. The emulsion is analysed and gives the results as given in table 1.

Example 4

Invention

Emulsion C is made by the same method as emulsion B except that the nucleation peptiser is replaced by the biopolymer of the invention (type H, example 1). The emulsion is analysed and gives the results as given in table 1.

Example 5

Comparative

Emulsion D is made by the same method as emulsion A except that the nucleation is performed at a pH of 6.0. The emulsion is analysed and gives the results as given in table 1.

Example 6

Comparative

Emulsion E is made by the same method as emulsion A except that the pH during the nucleation is increased from 3.5 to 6.0. The emulsion is analysed and gives the results as given in table 1.

Example 7

Invention

Emulsion F is made by the same method as emulsion D except that the nucleation peptiser is replaced by the biopolymer of the invention (type H) and that the nucleation is performed at a temperature of 15° C. The emulsion is analysed and gives the results as given in table 1.

Example 8

Invention

Emulsion G is made by the same method as emulsion E except that the nucleation peptiser is replaced by the biopolymer of the invention (type H) and that the nucleation is performed at a temperature of 15° C. The emulsion is analysed and gives the results as given in table 1.

Example 9

Comparative

Emulsion H is made by the same method as emulsion A except that the quantity of growth peptiser is reduced to 4 g. The emulsion is analysed and gives the results as given in table 1.

Example 10

Invention

Emulsion J is made by the same method as emulsion C except that the growth peptiser is replaced by the biopolymer of the invention (type H). The emulsion is analysed and gives the results as given in table 1.

TABLE 1

Analysis results of the produced emulsions

| Emulsion | % tabular crystals of total projected area | number % of non-parallelly twinned crystals | average aspect ratio | average size (weight average, nm) | coefficient of variation |
|---|---|---|---|---|---|
| A (comp.) | 90 | 10 | 6 | 470 | 31 |
| B (comp.) | 80 | 26 | 3 | 525 | 36 |
| C (inv.) | 93 | 6 | 5 | 350 | 24 |
| D (comp.) | 92 | 5 | 8 | 580 | 35 |
| E (comp.) | 92 | 7 | 7 | 555 | 32 |
| F (inv.) | 96 | 1 | 9 | 390 | 22 |
| G (inv.) | 93 | 3 | 7 | 245 | 18 |
| H (comp.) | 60 | 55 | 2 | 645 | 42 |
| J (inv.) | 93 | 8 | 6 | 360 | 23 |

Conclusions

Form these results can be concluded that by using the biopolymer of the invention a much smaller size of tabular crystals can be achieved with the same quality, which widens the scope of application. Also it is clear from the results that a much lower quantity of growth peptiser is required to provide a good steric protection during the growth step which enables a significant cost down in the usage of the biopolymer. It must be remarked that these examples are merely given to show the benefit of the invention and by no means are fully optimised for usage in an actual photographic product.

Example 11

Comparative

The biopolymer of the invention is hydrolysed by trypsin at a pH of 8 resulting in a polymer with the same binding region A as in the original compound but with a region B of reduced length. In stead of a hydrophilic tail of 109 amino acids long a tail of only 14 amino acids is present. Emulsion K is made by the same method as emulsion C but with the hydrolysed bio-polymer in stead of the original material. The analysis shows a severe coagulation indicating that a short tail is not able to give sufficient steric protection during the nucleation and/or the ripening.

Example 12

Comparative

A commercially available peptide, anti-sauvagine, characterised by a binding region A containing 1 His and 1 Met being 6 amino acids large and a hydrophilic region B with an average TFE of −3.9 and 23 amino acids large. This peptide is not a biopolymer according the invention because region B is too small; it is not collagen-like. Emulsion L is made with this biopolymer as growth peptiser by the same method as emulsion J. Analysis showed that this emulsion shows severe coagulation which indicates that the peptide used is not giving the steric protection that is achieved with a polymer according the invention.

Example 13

Comparative

A collagen-like biopolymer characterised by a binding region A containing 4 Met and 1 His and 123 aa large and a region B of hydrophilic character (av. TFE=−1.1) and 188 aa large, is used for making emulsion M by the same method as emulsion C. This polymer is not a biopolymer according the invention because region A is too large. Analysis shows that a very low percentage of tabular crystals is formed (<20% of the total surface area) indicating that a polymer with a too large binding area A is not effective as nucleation peptiser.

The invention claimed is:

1. A silver halide emulsion containing a nucleation peptiser, said nucleation peptiser being a polypeptide comprising:

at least one region A(n) having a maximum length of 100 amino acids, said region A(n) either (i) being delimited by the extreme two of at least two silver-binding amino acids selected from histidine, lysine and arginine, or (ii) being defined by the maximum stretch of amino acids having a polarity corresponding to an average transfer free energy ΔF equal to or higher than +1.0 kcal/mol, said maximum stretch containing at least 9 amino acids; and at least one region B(n) comprising at least 50 amino acids and having a polarity corresponding to an average transfer free energy ΔF equal to or lower than −1.0 kcal/mol and not containing histidine and, if lysine or arginine is among the silver-binding amino acids in region A(n), not containing lysine or arginine;

the polypeptide not containing methionine or cysteine.

2. A silver halide emulsion according to claim 1, wherein at least one region B(n) is a terminal region.

3. A silver halide emulsion according to claim 1, wherein region A(n)(i) contains at least two histidines.

4. A silver halide emulsion according to claim 1, wherein said region A(n)(i) has a polarity corresponding to an average transfer free energy ΔF equal to or higher than +0.5 kcal/mol.

5. A silver halide emulsion according to claim 1, wherein said region A(n)(i) comprises from 4 to 50 amino acids.

6. A silver halide emulsion according to claim 1, wherein a stretch of at least half said maximum length containing region A(n) does not contain silver-binding amino acids outside said region A(n).

7. A silver halide emulsion according to claim 1, wherein said at least one region B(n) is separated from region A(n).

8. A silver halide emulsion according claim 1, wherein said region B(n) has a polarity corresponding to an average transfer free energy equal to or lower than −1.3 kcal/mol.

9. A silver halide emulsion according to claim 1, wherein said region B(n) has a moving polarity corresponding to a moving average transfer free energy over 20 amino acids equal to or lower than +0.5 kcal/mol.

10. A silver halide emulsion according to claim 1, wherein said region B(n) comprises from 50 to 900 amino acids.

11. A silver halide emulsion according to claim 1, containing no more than two regions A(n).

12. A silver halide emulsion according to claim 1, wherein the polypeptide is collagen-like, comprising more than 50% amino acid triplets GXY, wherein G is glycine, and between 5 and 50% of X and Y are proline.

13. A silver halide emulsion according to claims 1, further comprising a growth peptiser, said growth peptiser being a polypeptide comprising:

at least one region A(g) containing at least two silver-binding amino acids and comprising more than 100 amino acids, up to a maximum of ⅓ part of the total number of amino acids, and at least one region B(g) comprising at least 50 amino acids having a polarity corresponding to an average transfer free energy ΔF equal to or lower than −0.5 kcal/mol and not comprising methionine residues.

14. A silver halide emulsion according to claim 13, wherein said region A(g) has a polarity corresponding to an average transfer free energy ΔF equal to or higher than +0.5 kcal/mol.

15. A silver halide emulsion according to claim 13, wherein at least one of said nucleation peptiser and said growth peptiser is a recombinant or synthetic polypeptide.

16. A silver halide emulsion according to claim 1, which is tabular.

17. A recombinant collagen-like polypeptide suitable as a nucleation peptiser at a pH higher than 5.0, comprising:

one or two regions A(n) having a maximum length of 100 amino acids, said region A(n) being delimited by the extreme two of at least two silver-binding histidines and the A(n) region comprising at least three silver-binding histidines; and at least one region B(n) (separated from regions A(n)) comprising at least 50 amino acids and having a polarity corresponding to an average transfer free energy ΔF equal to or lower than −1.0 kcal/mol;

the polypeptide not containing methionine or cysteine.

18. A recombinant collagen-like polypeptide suitable as a nucleation peptiser at a pH higher than 8.0, said polypeptide comprising:

one or two regions A(n) having a maximum length of 100 amino acids, said region A(n) (i) being delimited by the extreme two of at least two silver-binding amino acids selected from histidine, and arginine, and if said two silver binding amino acids are histidine then the A(n) region comprising at least three silver-binding histidines;

at least one region B(n) (separated from regions A(n)) comprising at least 50 amino acids and having a polarity corresponding to an average transfer free energy equal to or lower than −1.0 kcal/mol;

the polypeptide not containing methionine or cysteine.

19. A recombinant collagen-like polypeptide suitable as a nucleation peptiser at a pH of lower than 5.5, said polypeptide comprising:

one or two regions A(n) having a maximum length of 100 amino acids, said region A(n) being delimited by the extreme two of four silver-binding methionines, and at least one region B(n) (separated from regions A(n)) comprising at least 50 amino acids and having a polarity corresponding to an average transfer free energy equal to or −1.0 kcal/mol;

the polypeptide not containing methionine outside region A(n) and not containing cysteine.

20. A recombinant collagen-like polypeptide suitable as a growth peptiser, comprising:

one or two regions A(g) comprising more than 100 amino acids, up to a maximum of ⅓ part of the total number of amino acids, consisting of at least two silver-binding amino acids and at least 99 amino acids between the extreme two of said silver-binding amino acids, said at least two silver-binding amino acids comprising no more than two methionine residues, and/or at least two histidine residues, and at least one region B(g) (separated from regions A(g)) comprising at least 200 amino acids and having a polarity corresponding to an average transfer free energy equal to or lower than −1.0 kcal/mol and the polypeptide not containing methionine outside region A(g) and not containing cysteine.

21. A recombinant collagen-like polypeptide according to claim 17, wherein said region A(n) has a polarity corresponding to an average transfer free energy ΔF higher than 0 kcal/mol.

22. A recombinant collagen-like polypeptide suitable as a nucleation peptiser at a pH higher than 5.0, comprising:

only one region A(n) having a maximum length of 100 amino acids, said region A(n) being delimited by the extreme two of at least two silver-binding histidines, and at least one region B(n) being separated from region A(n), comprising at least 50 amino acids and having a polarity corresponding to an average transfer free energy ΔF equal to or lower than −1.0 kcal/mol;

the polypeptide not containing methionine or cysteine.

23. A recombinant collagen-like polypeptide according to claim 18, wherein said region A(n) has a polarity corresponding to an average transfer free energy ΔF higher than 0 kcal/mol.

24. A recombinant collagen-like polypeptide according to claim 19, wherein said region A(n) has a polarity corresponding to an average transfer free energy ΔF higher than 0 kcal/mol.

* * * * *

UNITED STATES PATENT AND TRADEMARK OFFICE

CERTIFICATE OF CORRECTION

PATENT NO. : 7,179,885 B2 
APPLICATION NO. : 10/451897
DATED : February 20, 2007
INVENTOR(S) : Jan Bastiaan Bouwstra It is certified that error appears in the above-identified patent and that said Letters Patent is hereby corrected as shown below:

On the title page, item (74), the spelling of the word "Kilpatrick" in the name of the firm should be changed to --Kirkpatrick--.

Signed and Sealed this

Seventeenth Day of April, 2007

JON W. DUDAS
*Director of the United States Patent and Trademark Office*